United States Patent [19]
Friese et al.

[11] Patent Number: 6,018,982
[45] Date of Patent: Feb. 1, 2000

[54] GAS-PERMEABLE CONNECTING LEAD FOR A PROBE

[75] Inventors: Karl-Hermann Friese, Leonberg; Helmut Weyl, Schwieberdingen; Anton Hans, Stuttgart, all of Germany

[73] Assignee: Robert Bosch GmbH, Stuttgart, Germany

[21] Appl. No.: 09/051,099

[22] PCT Filed: Jul. 24, 1997

[86] PCT No.: PCT/DE97/01562

§ 371 Date: May 26, 1998

§ 102(e) Date: May 26, 1998

[87] PCT Pub. No.: WO98/05951

PCT Pub. Date: Feb. 12, 1998

[30] Foreign Application Priority Data

Aug. 3, 1996 [DE] Germany ............................ 196 31 501

[51] Int. Cl.[7] ......................... G01N 27/407; G01N 27/26
[52] U.S. Cl. ...................... 73/23.2; 73/23.32; 73/31.05; 204/424; 204/410; 422/83
[58] Field of Search ................... 73/23.2, 23.31, 73/23.32, 23.34; 204/427, 424, 432, 410, 415

[56] References Cited

U.S. PATENT DOCUMENTS

| | | | |
|---|---|---|---|
| 3,714,015 | 1/1973 | Niedrach | 204/195 P |
| 3,873,267 | 3/1975 | Swartz | 23/230 B |
| 3,923,626 | 12/1975 | Niedrach et al. | 204/195 R |
| 4,221,567 | 9/1980 | Clark et al. | 23/230 B |
| 4,249,156 | 2/1981 | Micheli | 338/34 |
| 4,399,099 | 8/1983 | Buckles | 422/58 |
| 4,574,627 | 3/1986 | Sakurai et al. | 73/116 |
| 4,634,514 | 1/1987 | Nishizawa et al. | 204/406 |
| 4,974,929 | 12/1990 | Curry | 350/96.29 |
| 5,114,561 | 5/1992 | Bannister | 204/421 |
| 5,296,112 | 3/1994 | Seger et al. | 204/153.18 |
| 5,310,471 | 5/1994 | Markle et al. | 204/415 |
| 5,490,490 | 2/1996 | Weber et al. | 123/697 |

*Primary Examiner*—Hezron Williams
*Assistant Examiner*—J. David Wiggins
*Attorney, Agent, or Firm*—Kenyon & Kenyon

[57] ABSTRACT

A Lambda probe type gas sensor for use in determining the oxygen content of exhaust gases produced by an internal combustion engine includes a sensor element of the electrochemical, solid electrolyte, metallic oxide semiconductor or Lambda air-fuel ratio variety, which sensor element is arranged in a metallic housing and is contacted by connecting cables that are brought out of the metallic housing. These connecting cables are each surrounded by cable insulation that is made of PTFE (Polytetrafluoroethylene). The surface of the cable insulation has, at least in certain areas, a gas-permeable section that allows a reference atmosphere to arrive inside the cable insulation and, from there, in the metallic housing. The gas-permeable section, on the other hand, prevents ingress of liquids such as fuel, condensed water, etc., This is achieved, for example, by an additionally applied, PTFE film that is placed over the gas-permeable section.

8 Claims, 1 Drawing Sheet

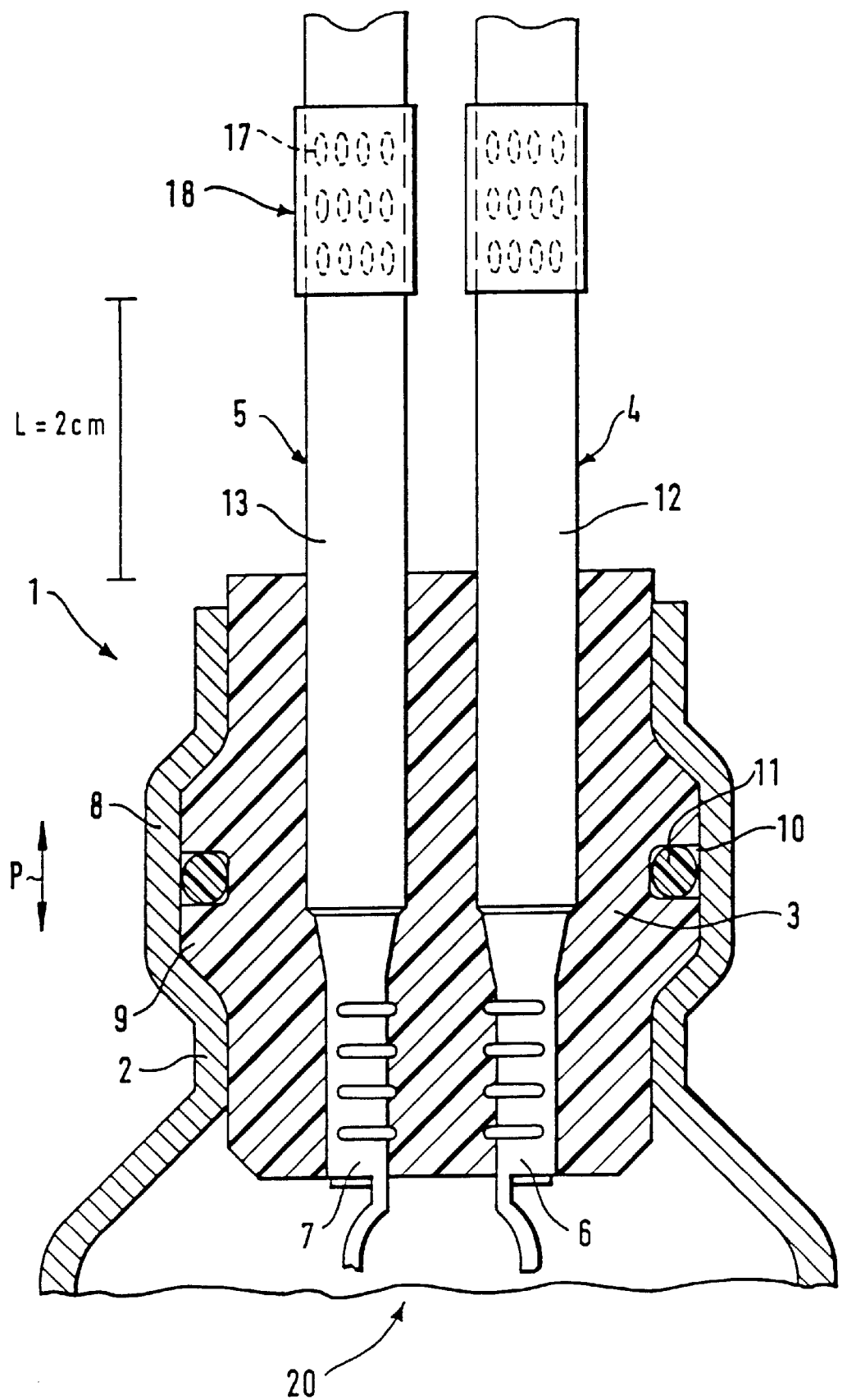

GAS-PERMEABLE CONNECTING LEAD FOR A PROBE

BACKGROUND INFORMATION

The present invention is directed to a sensor, for determining the oxygen content of exhaust gases produced by internal combustion engines to. The German Published Unexamined Application No. DE-OS 27 02 432 discloses a Lambda probe type gas sensor of this type, for example, where the reference air is introduced via a connecting cable into the housing, and the cavities disposed in the connecting cable insulation are not always sufficient to conduct enough reference air into the interior of the sensor's housing. One has to consider here that this reference air must be renewed at regular intervals, i.e., it must be coupled to the ambient air. On the other hand, to achieve unbiased measuring results, it is absolutely necessary that the reference air not come in contact with the exhaust gas to be measured, or e.g., with dirt, water, oil or gasoline from the ambient air. According to today's state of technological development, reference air is coupled to ambient air by way of a cable core, i.e., by way of the inner stranded conductor of the measuring cable, e.g., from the control unit. When the cable is lead through the measuring probe, the insulation sheath of the measuring cable must be sealed off absolutely imperviously. This process of leading the cable through is quite complex, since it requires manufacturing and assembling various components. This complexity is reflected accordingly in the manufacturing costs.

SUMMARY OF THE INVENTION

The connecting line according to the present invention has the advantage of enabling an improved supplying of reference atmosphere into the housing. The orifices placed in the sheath surface of the cable covering made of PTFE are sized to permit a sufficient quantity of reference air to penetrate through these gas-permeable sections to the inside of the cable covering and, from there, into the housing on the other hand, these gas permeable sections prevent the ingress of liquids, such as fuel, water, etc. It is particularly beneficial from a standpoint of production engineering, for the cable insulation to have orifices which are sheathed by an additional PTFE film, the PTFE film being pretreated to have a porosity which will, in fact, allow gas to arrive inside the housing, but not liquids or moisture or impurities. Since the additional PTFE film can be modified in different ways, one can advantageously adjust its specific permeability, through proper treatment, to hinder or prevent the otherwise critical diffusion of liquid hydrocarbon compounds. The additional PTFE film is advantageously shrink-fit onto the gas-permeable section of the PTFE line.

BRIEF DESCRIPTION OF THE DRAWING

An exemplary embodiment of the invention is shown in the drawing and elucidated in the following description. The only Figure shows a section through a cable sleeve, with the connecting cable of the present invention built into a lambda probe.

DETAILED

The figure shows a cross-section through the terminal side of a sensor 1, for example a lambda probe. This terminal side includes a housing 2 (partially shown), in which a sensor element 20 (not shown) is fixed in a gas-tight manner. Sleeve body 3 is disposed within housing 2. Two connecting cables 4, 5 extend right through sleeve body 3 and are provided at their lower end with crimp contacts 6, 7. Insulation sheaths 12, 13 are joined with form locking along their entire periphery to sleeve body 3. Placed at a distance L of, for example, 2 cm from housing 2 on the insulation sheaths 12, 13 are orifices 17, which are covered by an additional porous PTFE film 18, forming a traversing air-exchange channel between the sensor (not shown) and the outside air. Because insulation sheaths 12, 13 are permanently joined to sleeve body 3, all deformations in response to heating or cooling of sleeve body 3 are coupled to insulation sheaths 12, 13. Sleeve body 3 is secured by caulking in housing 2, which is why housing 2 has a toroidally-shaped protrusion 8, and sleeve body 3 has a torus 9 which fits into protrusion 8 and includes a groove 10. An O-ring 11 is inserted into groove 10. Insulation sheaths 12, 13 of connecting cables 4, 5 fit with form locking on sleeve body 3, and are permanently joined thereto.

During operation of the lambda probe, temperatures of between 250 through 280° C. arise at the cable outlet. When sleeve body 3, which is made of Teflon-filled fiber glass, undergoes thermal expansion, it expands axially, i.e., in the direction of double arrow P, since it is securely enclosed in the radial direction by metal sleeve 2. In response to cooling, sleeve body 3 does not completely return to its original form. To assure an impervious connection in this case, groove 10 is provided with an inner Witon-O-ring 11. The described arrangement is heated, for example in an oven, causing sleeve body 3 as well as insulation sheaths 12, 13 to expand. Any existing annular gaps around insulation sheaths 12, 13 are closed in the process. As a result, only gas can still arrive via orifices 17 inside the sensor (not shown).

The additional, porous PTFE film 18 is produced by stretching the PTFE material using a generally known method. It is likewise conceivable, however, to make this PTFE film 18 permeable to air by mechanically applying very fine pin holes. Moreover, it is conceivable to make the PTFE material of insulation sheaths 12, 13 porous, at least in certain areas, by stretching the material in a generally known manner.

We claim:

1. A Lambda probe type gas sensor for determining an oxygen content of exhaust gases produced by an internal combustion engine, comprising:
    a metallic housing;
    a sensor element arranged in the housing; and
    at least one connecting cable in electrical contact with the sensor element and surrounded by a cable insulation, wherein at least a portion of the at least one connecting cable is outside of the housing, wherein a reference atmosphere for the sensor element is introduced into the housing, and wherein at least a portion of a surface of the cable insulation includes at least one gas-permeable section for permitting the reference atmosphere to arrive inside the cable insulation and flow to the housing.

2. The sensor according to claim 1, wherein the at least one gas-permeable section includes orifices through which the reference atmosphere arrives inside the cable insulation.

3. The sensor according to claim 2, wherein the orifices are arranged at least 1 cm outside of the housing.

4. The sensor according to claim 2, wherein the cable insulation is enveloped in an area of the orifices by a gas-permeable PTFE-film.

5. The sensor according to claim 4, wherein the PTFE-film is porous.

6. The sensor according to claim 5, wherein a porosity of the PTFE-film allows at least one of an ingress and a diffusion of only a gas, but not a liquid.

7. The sensor according to claim 6, wherein the liquid includes one of a fuel and condensed water.

8. The sensor according to claim 1, wherein the cable insulation is made of PTFE.

* * * * *

UNITED STATES PATENT AND TRADEMARK OFFICE
CERTIFICATE OF CORRECTION

PATENT NO. : 6,018,982
DATED : February 1, 2000
INVENTOR(S) : Friese et al.

It is certified that error appears in the above-identified patent and that said Letters Patent is hereby corrected as shown below:

Col. 1, line 8, delete "to"

Col. 1, line 39, delete "housing on the other hand" and insert --housing. On the other hand--

Col. 1, line 55, delete "An exemplary embodiment of the invention is shown in the drawing and elucidated in the following description. The only Figure shows a section through a cable sleeve, with the connecting cable of the present invention built into a lambda probe." and insert --The Figure shows a section through a cable sleeve, with the connecting cable of the present invention being built into a lambda probe.--

Col. 1, line 61, delete "DETAILED" and insert --DETAILED DESCRIPTION--

Col. 2, line 7, delete ", forming" and insert --. Orifices 17 and additional porous PTFE film 18 form--

Signed and Sealed this

Fifteenth Day of May, 2001

Attest:

*Attesting Officer*

NICHOLAS P. GODICI

*Acting Director of the United States Patent and Trademark Office*